United States Patent [19]

Kamioka et al.

[11] 4,450,162
[45] May 22, 1984

[54] PYRIMIDINE DERIVATIVES AND A PHARMACEUTICAL COMPOSITION CONTAINING THEM

[75] Inventors: Toshiharu Kamioka; Isao Nakayama, both of Hiromachi; Takeo Honda, Ube; Takashi Kobayashi, Ube; Tokio Obata, Ube; Katsutoshi Fujii, Ube; Mikio Kojima, Ube; Yuji Akiyoshi, Ube, all of Japan

[73] Assignees: Sankyo Company, Limited, Tokyo; Ube Industries Limited, Ube, both of Japan

[21] Appl. No.: 384,416

[22] Filed: Jun. 2, 1982

[30] Foreign Application Priority Data

Jun. 5, 1981 [JP] Japan .................................. 56-86555

[51] Int. Cl.³ .................. A61K 31/505; C07D 239/42
[52] U.S. Cl. .................................. 424/251; 544/253; 544/326; 544/327; 544/329
[58] Field of Search ............... 544/326, 329, 327, 253; 424/251

[56] References Cited

U.S. PATENT DOCUMENTS 3,321,478  5/1967  English et al. ....................... 544/326
3,978,055  8/1976  Fauran et al. ....................... 544/326
4,362,874 12/1982  Kalk et al. .......................... 544/327

*Primary Examiner*—Donald G. Daus
*Assistant Examiner*—James H. Turnipseed
*Attorney, Agent, or Firm*—Frishauf, Holtz, Goodman & Woodward

[57] ABSTRACT

New 4-anilinopyrimidine derivatives of formula (I):

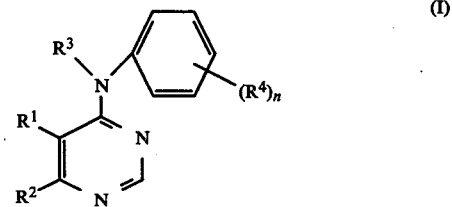

(wherein:

$R^1$ and $R^2$ are the same or different and each represents a $C_1$–$C_6$ alkyl group or $R^1$ and $R^2$ together represent a $C_3$–$C_5$ alkylene group;

$R^3$ represents a hydrogen atom or a $C_1$–$C_6$ alkyl group;

n is 0, 1 or 2; and $R^4$ represents a $C_1$–$C_6$ alkyl group, a $C_1$–$C_6$ alkoxy group, a $C_1$–$C_6$ haloalkyl group, a halogen atom, a nitro group, a $C_1$–$C_6$ alkanesulphonyl group, a cyano group, a carboxy group or a $C_2$–$C_7$ alkoxycarbonyl group and, when n is 2, the two groups represented by $R^4$ may be the same or different or they may together represent a methylenedioxy group)

and pharmaceutically acceptable acid addition salts thereof have been found to have strong antidepressant activity, with low toxicity and very few side-effects. The compounds may be formulated in conventional pharmaceutical compositions for administration by various routes and may be prepared by reacting a 4-halopyrimidine with aniline or an aniline derivative.

11 Claims, No Drawings

PYRIMIDINE DERIVATIVES AND A PHARMACEUTICAL COMPOSITION CONTAINING THEM

BACKGROUND TO THE INVENTION

The present invention relates to a series of new 4-anilinopyrimidine derivatives having valuable antidepressant activity, to a process for preparing these compounds and to a pharmaceutical composition containing them.

A variety of compounds having antidepressant activity is known and many of these are used in the treatment of mental depression. The compounds mainly used for this purpose are commonly classified into two groups: the "monoamine oxidase inhibitors", which are mostly hydrazine derivatives; and the "tricyclic antidepressants", which mainly have a dibenzazepine or dibenzocycloheptene structure ["Martindale: The Extra Pharmacopoeia", twenty-seventh Edition (1977), published by The Pharmaceutical Press, London]. Of these classes, the tricyclic antidepressants are generally considered to be more effective than the monoamine oxidase inhibitors and are therefore preferred; one of the most preferred of the tricyclic antidepressants in current use is imipramine. All of the currently available antidepressants exhibit a variety of side-effects of varying degrees of seriousness which result in their use being somewhat restricted. Imipramine, for example, exhibits antihistaminic and anticholinergic activities.

The known classes of antidepressant, however, have a totally different molecular structure from the compounds of the invention.

A compound having a structure similar to that of the compounds of the invention, namely 4-anilino-5-bromo-6-methylpyrimidine, has been disclosed [Chem. Pharm. Bull. Tokyo, 27 (11), 2642–6 (1979)] but no use for the compound has been disclosed nor has it been disclosed that the compound exhibits any pharmaceutical activity. We have subsequently confirmed that this compound shows no antidepressant activity. Indeed, we know of no pyrimidine derivatives similar to the compounds of the invention which exhibit any such antidepressant activity.

BRIEF SUMMARY OF INVENTION

It is, therefore, an object of the present invention to provide a series of new 4-anilinopyrimidine derivatives having antidepressant activity.

It is a further, and more specific, object of the invention to provide such compounds having reduced toxicity and side-effects.

Still further objects of the invention include the provision of a process for preparing the compounds of the invention and pharmaceutical compositions containing these compounds.

The compounds of the invention are those 4-anilinopyrimidine derivatives having the formula (I):

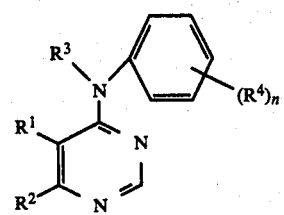

(wherein:
$R^1$ and $R^2$ are the same or different and each represents a $C_1$–$C_6$ alkyl group or $R^1$ and $R^2$ together represent a $C_3$–$C_5$ alkylene group;

$R^3$ represents a hydrogen atom or a $C_1$–$C_6$ alkyl group;

n is 0, 1 or 2; and $R^4$ represents a $C_1$–$C_6$ alkyl group, a $C_1$–$C_6$ alkoxy group, a $C_1$–$C_6$ haloalkyl group, a halogen atom, a nitro group, a $C_1$–$C_6$ alkanesulphonyl group, a cyano group, a carboxy group or a $C_2$–$C_7$ alkoxycarbonyl group and, when n is 2, the two groups represented by $R^4$ may be the same or different or they may together represent a methylenedioxy group), and pharmaceutically acceptable acid addition salts thereof.

These compounds may be prepared by reacting a halopyrimidine derivative of formula (II):

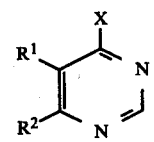

(wherein $R^1$ and $R^2$ are as defined above and X represents a halogen atom) with aniline or an aniline derivative of formula (III):

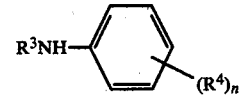

(wherein $R^3$, $R^4$ and n are as defined above).

The invention also provides a pharmaceutical composition comprising an effective amount of an antidepressant in admixture with a pharmaceutically acceptable carrier or diluent, wherein the antidepressant is at least one compound of formula (I), as defined above, or a pharmaceutically acceptable acid addition salt thereof.

DETAILED DESCRIPTION OF THE INVENTION

In the compounds of the invention, when $R^1$ and $R^2$ represent alkyl groups, these may be the same or different and the groups may be straight or branched chain groups. They preferably have from 1 to 4 carbon atoms and examples of such groups include the methyl, ethyl, propyl, isopropyl, butyl and isobutyl groups, more preferably methyl or ethyl groups. Alternatively, $R^1$ and $R^2$ together may represent an alkylene group, which preferably has 3 or 4 carbon atoms, for example a trimethylene, propylene or tetramethylene group; of those compounds where $R^1$ and $R^2$ together represent an alkylene group, the most preferred are compounds of formula (Ia):

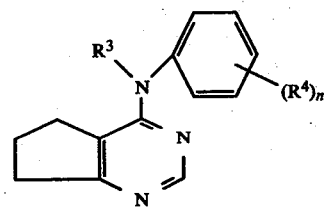

(wherein $R^3$, $R^4$ and n are as defined above).

$R^3$ may represent a hydrogen atom or an alkyl group, which may be a straight or branched chain group and preferably has from 1 to 3 carbon atoms, that is to say the methyl, ethyl, propyl and isopropyl groups.

Where $R^4$ represents an alkyl group, this may be a straight or branched chain group and preferably has from 1 to 4 carbon atoms; examples include the methyl, ethyl, propyl, isopropyl, butyl and isobutyl groups. Where $R^4$ represents an alkoxy group, this may be a straight or branched chain group and preferably has from 1 to 4 carbon atoms; examples include the methoxy, ethoxy, propoxy, isopropoxy, butoxy and isobutoxy groups.

Where $R^4$ represents a haloalkyl group, the alkyl group may be a straight or branched chain group and preferably has from 1 to 3 carbon atoms, for example a methyl, ethyl, propyl or isopropyl group, more preferably the methyl group. The halogen atom may be fluorine, chlorine, bromine or iodine, preferably fluorine. There may be one or more halogen atoms, preferably three halogen atoms. The most preferred such group is the trifluoromethyl group.

Where $R^4$ represents a halogen atom, this may be a fluorine, chlorine, bromine or iodine atom. Where $R^4$ represents an alkanesulphonyl group, the alkyl group may be straight or branched chain and preferably has from 1 to 3 carbon atoms; examples of such groups include the methanesulphonyl, ethanesulphonyl and propanesulphonyl groups. Where $R^4$ represents an alkoxycarbonyl group, this preferably has from 2 to 4 carbon atoms and examples include the methoxycarbonyl, ethoxycarbonyl, propoxycarbonyl and isopropoxycarbonyl groups.

When n is 2, the two atoms or groups represented by $R^4$ may then be the same or different. Alternatively, when n is 2, the two groups represented by $R^4$ may then together form a methylenedioxy group.

A more preferred group of compounds of the present invention are those in which:

$R^1$ represents a methyl group, an ethyl group or a butyl group and $R^2$ represents a methyl group, or
$R^1$ and $R^2$ together represent a trimethylene group;
$R^3$ represents a hydrogen atom;
n is 0, 1 or 2; and
when n is 1, $R^4$ is at the 4-position of the benzene ring and represents an ethyl group, an isopropyl group, a trifluoromethyl group, a fluorine atom, a chlorine atom, a bromine atom, an iodine atom, a nitro group, a methanesulphonyl group, a cyano group, a carboxy group, a methoxycarbonyl group or an ethoxycarbonyl group;
when n is 2, both $R^4$ represent chlorine atoms at the 3 and 4 positions of the benzene ring.

The most preferred compounds of the invention are those in which:

$R^1$ represents a methyl group, an ethyl group or a butyl group and $R^2$ represents a methyl group, or
$R^1$ and $R^2$ together represent a trimethylene group;
$R^3$ represents a hydrogen atom;
n is 0 or 1; and
when n is 1, $R^4$ is at the 4-position of the benzene ring and represents an ethyl group, an isopropyl group, a fluorine atom, a chlorine atom, a bromine atom, an iodine atom, a cyano group or a methanesulphonyl group, most preferably a chlorine atom, a bromine atom or a cyano group.

The compounds of formula (I) will form acid addition salts and these salts, when pharmaceutically acceptable, also form part of the present invention. The salts may be with an inorganic acid, for example hydrochloric acid, hydrobromic acid or hydroiodic acid, or with an organic acid, for example oxalic acid, maleic acid, fumaric acid, tartaric acid or citric acid. The hydrochloric acid salts are particularly convenient.

Examples of the compounds of the invention are given in the following list; the numbers appended to the compounds in this list are used hereinafter to identify them:

1. 4-Anilino-6,7-dihydro-5H-cyclopenta[d]pyrimidine.
2. 4-Anilino-6,7-dihydro-5H-cyclopenta[d]pyrimidine hydrochloride.
3. 4-(4-Chloroanilino)-6,7-dihydro-5H-cyclopenta[d]pyrimidine.
4. 4-(4-Fluoroanilino)-6,7-dihydro-5H-cyclopenta[d]pyrimidine.
5. 4-(4-Bromoanilino)-6,7-dihydro-5H-cyclopenta[d]pyrimidine.
6. 4-(4-Iodoanilino)-6,7-dihydro-5H-cyclopenta[d]pyrimidine.
7. 4-(4-Iodoanilino)-6,7-dihydro-5H-cyclopenta[d]pyrimidine hydrochloride.
8. 4-p-Toluidino-6,7-dihydro-5H-cyclopenta[d]pyrimidine.
9. 4-(4-Ethylanilino)-6,7-dihydro-5H-cyclopenta[d]pyrimidine.
10. 4-(4-Isopropylanilino)-6,7-dihydro-5H-cyclopenta[d]pyrimidine
11. 4-(4-Trifluoromethylanilino)-6,7-dihydro-5H-cyclopenta[d]pyrimidine.
12. 4-(4-Nitroanilino)-6,7-dihydro-5H-cyclopenta[d]pyrimidine
13. 4-(4-Nitroanilino)-6,7-dihydro-5H-cyclopenta[d]pyrimidine hydrochloride
14. 4-(4-Cyanoanilino)-6,7-dihydro-5H-cyclopenta[d]pyrimidine
15. 4-(4-Methanesulphonylanilino)-6,7-dihydro-5H-cyclopenta[d]pyrimidine
16. 4-(4-Methoxyanilino)-6,7-dihydro-5H-cyclopenta[d]pyrimidine
17. 4-(4-Ethoxyanilino)-6,7-dihydro-5H-cyclopenta[d]pyrimidine
18. 4-(4-Carboxyanilino)-6,7-dihydro-5H-cyclopenta[d]pyrimidine
19. 4-(4-Methoxycarbonylanilino)-6,7-dihydro-5H-cyclopenta[d]pyrimidine
20. 4-(4-Ethoxycarbonylanilino)-6,7-dihydro-5H-cyclopenta[d]pyrimidine
21. 4-(3,4-Methylenedioxyanilino)-6,7-dihydro-5H-cyclopenta[d]pyrimidine
22. 4-Anilino-5,6-dimethylpyrimidine
23. 4-Anilino-5,6-dimethylpyrimidine hydrochloride
24. 4-(3-Chloroanilino)-5,6-dimethylpyrimidine
25. 4-(4-Chloroanilino)-5,6-dimethylpyrimidine 26. 4-(2-Bromoanilino)-5,6-dimethylpyrimidine
27. 4-(3-Bromoanilino)-5,6-dimethylpyrimidine
28. 4-(4-Bromoanilino)-5,6-dimethylpyrimidine
29. 4-(2-Fluoroanilino)-5,6-dimethylpyrimidine
30. 4-(3-Fluoroanilino)-5,6-dimethylpyrimidine
31. 4-(4-Fluoroanilino)-5,6-dimethylpyrimidine
32. 4-(4-Iodoanilino)-5,6-dimethylpyrimidine
33. 4-(2,4-Dichloroanilino)-5,6-dimethylpyrimidine
34. 4-(3,4-Dichloroanilino)-5,6-dimethylpyrimidine
35. 4-(3,4-Dichloroanilino)-5,6-dimethylpyrimidine hydrochloride
36. 4-(3,5-Dichloroanilino)-5,6-dimethylpyrimidine
37. 4-(4-Chloro-3-trifluoromethylanilino)-5,6-dimethylpyrimidine
38. 5,6-Dimethyl(-4-(4-trifluoromethylanilino)pyrimidine
39. 4-(2-Methoxyanilino)-5,6-dimethylpyrimidine
40. 4-(3-Methoxyanilino)-5,6-dimethylpyrimidine
41. 4-(4-Methoxyanilino)-5,6-dimethylpyrimidine
42. 4-(2-Ethoxyanilino)-5,6-dimethylpyrimidine
43. 4-(3-Ethoxyanilino)-5,6-dimethylpyrimidine
44. 4-(4-Ethoxyanilino)-5,6-dimethylpyrimidine
45. 5,6-Dimethyl-4-p-toluidinopyrimidine
46. 4-(4-Ethylanilino)-5,6-dimethylpyrimidine
47. 4-(4-Isopropylanilino)-5,6-dimethylpyrimidine
48. 4-(4-Isopropylanilino)-5,6-dimethylpyrimidine hydrochloride
49. 4-(4-n-Butylanilino)-5,6-dimethylpyrimidine
50. 5,6-Dimethyl-4-(4-nitroanilino)pyrimidine
51. 4-(4-Methanesulphonylanilino)-5,6-dimethylpyrimidine
52. 4-(4-Cyanoanilino)-5,6-dimethylpyrimidine
53. 4-(4-Carboxyanilino)-5,6-dimethylpyrimidine
54. 4-(4-Carboxyanilino)-5,6-dimethylpyrimidine hydrochloride
55. 4-(4-Methoxycarbonylanilino)-5,6-dimethylpyrimidine
56. 4-(4-Ethoxycarbonylanilino)-5,6-dimethylpyrimidine
57. 5,6-Dimethyl-4-(N-methylanilino)pyrimidine
58. 5,6-Dimethyl-4-(N-methyl-p-toluidino)pyrimidine
59. 4-(4-Ethyl-N-methylanilino)-5,6-dimethylpyrimidine
60. 4-(4-Chloro-N-methylanilino)-5,6-dimethylpyrimidine
61. 4-Anilino-5-ethyl-6-methylpyrimidine
62. 4-(4-Chloroanilino)-5-ethyl-6-methylpyrimidine
63. 4-(4-Bromoanilino)-5-ethyl-6-methylpyrimidine
64. 5-Ethyl-4-(4-fluoroanilino)-6-methylpyrimidine
65. 5-Ethyl-4-(4-ethylanilino)-6-methylpyrimidine
66. 4-(4-Ethoxyanilino)-5-ethyl-6-methylpyrimidine
67. 4-Anilino-6-methyl-5-n-propylpyrimidine
68. 4-(4-Ethylanilino)-6-methyl-5-n-propylpyrimidine
69. 4-(4-Bromoanilino)-5-n-butyl-6-methylpyrimidine
70. 4-(4-Bromoanilino)-5,6-diethylpyrimidine
71. 4-(4-Bromoanilino)-5,6-diethylpyrimidine hydrochloride.

Of the compounds listed above, the most preferred are Compounds No. 14, 28 and 69.

The compounds of the invention show excellent antidepressant activity, combined with low toxicity and few side-effects; these properties are demonstrated by the following tests:

1 Test for anti-reserpine activity

The test animals used were male mice of the ddy strain, each weighing 23-25 g. Each compound was tested on a group of three such mice. Each test compound was employed in the form of a solution or suspension in a physiological saline solution containing 0.3% w/v carboxymethylcellulose. The test employed was a partial modification of the method of Rubin et al. [J. Pharmacol. Exptl. Therap., 120, 125 (1957)].

2 mg/kg of reserpine was injected subcutaneously into each mouse and, immediately after the injection, the solution or suspension of the test compound was given orally in a dose of 50 mg/kg for all compounds except Compound No. 14, which was given in a dose of 25 mg/kg. The animals were observed 90 minutes, 120 minutes and 180 minutes after administration to evaluate the inhibition of ptosis. At each observation, each mouse was assigned from 0 to 3 points corresponding to the degree of ptosis, as follows:

0 points: eyes completely open;
1 point: eyes about one third closed;
2 points: eyes about two thirds closed;
3 points: eyes completely closed.

For each mouse, the number of points from all three observations were added together and the percentage inhibition of reserpine-induced ptosis was calculated from the following formula:

$$\text{Reserpine inhibition percentage} = \left( \frac{P_o - P_t}{P_o} \right) \times 100$$

in which:

$P_o$ = total number of points from three observations of an animal to which reserpine alone was administered; and $P_t$ = total number of points from three observations of an animal to which reserpine and the test compound were administered.

The results are shown in the following Table 1.

2. Potentiation of d-Amphetamine effects

The test animals used in this experiment were male rats of the Wistar strain, each weighing from 250 to 300 g. The rats were employed in groups of 4 animals each, for each test. The test compound was employed in the form of a solution or suspension in physiological saline containing 0.3% w/v carboxymethylcellulose. The test, to determine the degree of enhancement of the effects of d-amphetamine, was a modified version of the method of Costall et al. [Eur. J. Pharmacol., 18, 95 (1972)].

Each rat was placed in an observation cage and then given orally the solution or suspension of the test compound in an amount of 10 mg of test compound per kilogram body weight; 60 minutes later, 2.5 mg/kg of d-amphetamine sulphate were injected subcutaneously. The rats were observed 30 minutes, 60 minutes, 90 minutes, 120 minutes, 150 minutes, 180 minutes and 240 minutes after the injection of the d-amphetamine sulphate. At each observation, each animal was assigned from 0 to 5 points according to its mobility, as follows:

0 points: sedation;
1 point: slight moving around;
2 points: moving around;
3 points: sniffing appears;
4 points: licking appears;
5 points: biting appears.

The percentage potentiation of the effects of d-amphetamine was then calculated from the following formula:

$$\text{d-Amphetamine potentiation percentage} = \left(\frac{P_t' - P_o'}{P_o'}\right) \times 100$$

where:

$P'_o$ = total number of points from all observations of an animal to which d-amphetamine alone was administered; and $P'_t$ = total number of points from all seven observations of an animal to which both the test compound and d-amphetamine were administered.

The results are shown in Table 1.

TABLE 1

| Compound No | Reserpine inhibition (%) | d-Amphetamine potentiation (%) |
|---|---|---|
| 2 | 68.7 | — |
| 3 | 82.3 | — |
| 5 | 75.6 | — |
| 9 | 82.3 | — |
| 11 | 62.5 | — |
| 14 | 85.0 | — |
| 25 | 61.1 | 75 |
| 28 | 61.1 | 79 |
| 32 | 43.8 | 76 |
| 38 | 68.8 | — |
| 47 | 70.6 | — |
| 69 | — | 94 |
| Imipramine hydrochloride | 72.2 | 77 |

3. Acute toxicity test

The test animals used were male mice of the ddy strain, each weighing from 21 to 25 g. To each animal was administered orally a single dose of the test compound in the amount shown in Table 2; the animals were then placed under observation for 7 days after administration. The results are reported in Table 2 as "Mortality", where the numerator indicates the number of deaths in the observation period and the denominator indicates the number of animals tested with the particular test compound at the particular dose.

TABLE 2

| Compound No | Dose (mg/kg) | Mortality |
|---|---|---|
| 5 | 500 | 0/5 |
|   | 1000 | 0/5 |
| 28 | 1000 | 0/5 |
| Imipramine hydrochloride | 500 | 3/5 (2 within 1 hour; 1 on day 3) |

It is apparent from the results of the above tests that the compounds of the invention have excellent antidepressant activity combined with a low toxicity; what is more, few side-effects of the compounds of the invention were observed. The compounds may be administered for the treatment of mental depression orally (for example in the form of tablets, capsules, granules, powders or syrups) or parenterally (for example by subcutaneous or intravenous injection or as suppositories). The pharmaceutical composition may be prepared by formulating the active ingredient with vehicles known in the art to be useful for the preparation of such compounds, for example solubilising, suspending, diluting, binding, disintegrating, lubricating and/or flavouring agents.

The dose of the compound of the invention will vary, depending upon the condition and age of the patient and on the route of administration. For an adult human, the recommended daily dose would be from 20 mg to 500 mg, which can be administered as a single dose or in divided doses.

The compounds of formula (I) may be prepared by heating a halopyrimidine derivative of formula (II):

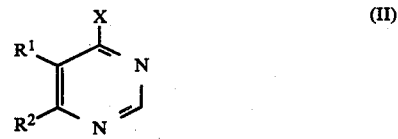

(in which $R^1$, $R^2$ and X are as defined above, X preferably being a chlorine, bromine or iodine atom) with aniline or an aniline derivative of formula (III):

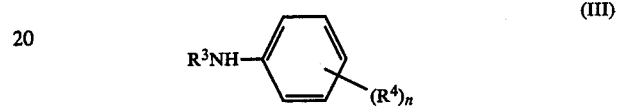

(in which $R^3$, $R^4$ and n are as defined above).

This reaction may be carried out in a variety of ways. For example, the halopyrimidine derivative of formula (II) may be mixed with at least an equimolar amount of the aniline compound of formula (III) and the mixture heated, with or without a solvent. Alternatively, at least an equimolar amount of the aniline compound of formula (III) may be added to a solution of the halopyrimidine derivative of formula (II) and the resulting solution heated. Where a solvent is employed, its nature is not particularly critical, provided that it has no adverse effect upon the reaction; suitable solvents include, for example, alcohols (such as methanol or ethanol), ethers (such as tetrahydrofuran or dioxan) and aromatic hydrocarbons (such as toluene or xylene). The reaction temperature is also not critical, but best results are generally achieved by employing a temperature of from 100° C. to 200° C. if no solvent is used or about the reflux temperature of the solvent if a solvent is present.

A catalytic amount of a mineral acid (such as hydrochloric acid or sulphuric acid) can be added to the reaction mixture in order to accelerate the reaction. The time required for the reaction will, of course, depend upon the nature of the reagents and on the presence or absence of the mineral acid, as well as upon the reaction temperature, but the reaction will generally be complete within 1 hour when the reaction is conducted without a solvent and within 24 hours when the reaction is conducted under reflux using a solvent.

Under the reaction conditions described above, the compounds of the invention are generally obtained in the form of a hydrohalic acid salt corresponding to the halogen atom represented by X in the halopyrimidine derivative of formula (II), although occasionally the compound of formula (I) in the free form may be obtained, if the aniline compound of formula (III) acts as an acid-binding agent.

Alternatively, in order to obtain the desired compound of formula (I) in the form of the free base, the reaction may be conducted by dissolving the halopyrimidine derivative of formula (II) in an organic solvent having a high boiling point (such as toluene, xylene or m-dichlorobenzene), adding to the solution at least an equimolar amount of the aniline compound of formula (III) and at least 1.2 times the molar amount of a base (such as triethylamine) and heating the mixture under reflux at about the boiling temperature of the solvent employed; the reaction will generally be complete within 24 hours.

After completion of the reaction, the compound of the invention may be recovered from the reaction mixture by conventional means, for example by leaving the reaction mixture to cool, collecting the resulting precipitate by filtration and then recrystallising it from a suitable organic solvent to give the desired compound, generally in the form of the hydrohalic acid salt. Where it is desired to obtain the compound in the form of the free base, the reaction mixture is first made alkaline by the addition of a base (such as an aqueous solution of sodium hydroxide) and it is then extracted with a water-immiscible organic solvent (such as ethyl acetate); the organic phase is then separated and dried and the solvent is distilled off under reduced pressure; finally, the resulting residue is recrystallised from a suitable organic solvent to give the desired product.

Where the compound is obtained in the form of its free base, it can, if necessary, be converted to a pharmaceutically acceptable acid addition salt by conventional salification methods.

The preparation of the compounds of the invention is further illustrated by the following Examples 1 to 7, whilst pharmaceutical compositions of the invention are illustrated in Examples 8 and 9.

EXAMPLE 1

4-Anilino-6,7-dihydro-5H-cyclopenta[d]pyrimidine hydrochloride (Compound No. 2)

To 3.1 g (0.02 mole) of 4-chloro-6,7-dihydro-5H-cyclopenta[d]pyrimidine were added 4.7 g (0.05 mole) of aniline and about 10 ml of ethanol; the mixture was then heated at 100° C. for about 10 minutes; the mixture quickly became a solution and then soon produced crystals. The mixture was then heated for a further 5 minutes, after which it was allowed to cool. The crystals produced were collected by filtration and then recrystallised from ethanol, to give 2.9 g (yield 59%) of the desired Compound No. 2, in the form of yellow needles melting at 220° C. (with decomposition).

Elemental analysis: Calculated for $C_{13}H_{14}N_3Cl$: C, 63.03%; H, 5.70%; N, 16.96%. Found: C, 63.30%; H, 5.80%; N, 16.85%.

EXAMPLE 2

4-(4-Chloroanilino)-6,7-dihydro-5H-cyclopenta[d]pyrimidine (Compound No. 3)

To 3.1 g (0.02 mole) of 4-chloro-6,7-dihydro-5H-cyclopenta[d]pyrimidine were added 5.1 g (0.04 mole) of p-chloroaniline and about 10 ml of ethanol; the mixture was then heated at 130° C. for 5-10 minutes. The reaction mixture quickly became a solution and then produced crystals of the hydrochloride of the desired product on being allowed to cool.

To the mixture were added 50 ml of a 2 N aqueous solution of sodium hydroxide, and then the mixture was stirred, to produce an oil. The mixture was then extracted with 200-300 ml of ethyl acetate and the extract was washed with water and dried over anhydrous sodium sulphate. The solvent was distilled off under reduced pressure and the resulting residue was recrystallised from a 4:1 by volume mixture of ethanol and water, to give 3.4 g (yield 69%) of the desired Compound No. 3, in the form of colourless needles melting at 204°-206° C.

Elemental analysis: Calculated for $C_{13}H_{12}N_3Cl$: C, 63.55%; H, 4.92%; N, 17.10%. Found: C, 63.50%; H, 4.90%; N, 17.10%.

Following the procedure described in Example 2, the compounds listed in Table 3 were also obtained.

TABLE 3

| Compound No | melting at (°C.) | Appearance | yield (%) |
|---|---|---|---|
| 4 | 180–182 | colourless prisms | 74 |
| 5 | 210–212 | colourless needles | 76 |
| 8 | 164–166 | colourless needles | 75 |
| 9 | 136–138 | colourless needles | 77 |
| 10 | 160–162 | colourless needles | 75 |
| 11 | 150–152 | pale brown prisms | 88 |
| 14 | 218–220 | pale brown prisms | 32 |
| 16 | 169–171 | colourless needles | 71 |
| 17 | 152–154 | colourless prisms | 67 |
| 21 | 209–211 | pale brown prisms | 53 |

EXAMPLE 3

4-(4-Chloroanilino)-5,6-dimethylpyrimidine (Compound No. 25)

To 4.3 g (0.03 mole) of 4-chloro-5,6-dimethylpyrimidine were added 3.8 g (0.03 mole) of p-chloroaniline and about 10 ml of ethanol; the mixture was then heated at 130° C. for about 3 minutes. The reaction mixture quickly became a solution and then the hydrochloride of the desired compound precipitated as the solution was allowed to cool. The crystals thus obtained were separated and ground to a powder and then made alkaline by the addition of a dilute aqueous solution of sodium hydroxide. The insolubles were collected by filtration, washed with water and dried. The resulting crystals were recrystallised from benzene, to give 4.2 g (yield 60%) of the desired Compound No. 25, in the form of colourless needles melting at 170°-173° C.

Elemental analysis: Calculated for $C_{12}H_{12}N_3Cl$: C, 61.67%; H, 5.14%; N, 17.98%. Found: C, 61.50%; H, 5.40%; N, 18.10%.

EXAMPLE 4

4-(4-Ethylanilino)-5,6-dimethylpyrimidine (Compound No. 46)

To 4.3 g (0.03 mole) of 4-chloro-5,6-dimethylpyrimidine were added 3.6 g (0.03 mole) of p-ethylaniline; the mixture was then heated at 150° C. for about 3 minutes. The reaction mixture quickly became a solution which, on cooling, precipitated crystals. These crystals were separated and then made alkaline by the addition of 50 ml of a dilute aqueous solution of sodium hydroxide. The insolubles were extracted with about 100 ml of ethyl acetate and the resulting extract was washed, in turn, with water and with a saturated aqueous solution of sodium chloride; it was then dried over anhydrous sodium sulphate. The ethyl acetate was distilled off under reduced pressure to give crystals, which were recrystallised from benzene, affording 4.8 g (yield 71%) of the desired Compound No. 46, in the form of colourless needles melting at 97°-98° C.

Elemental analysis: Calculated for $C_{14}H_{17}N_3$: C, 74.01%; H, 7.48%; N, 18.50%. Found: C, 74.10%; H, 7.50%; N, 18.10%.

EXAMPLE 5

4-(4-Isopropylanilino)-5,6-dimethylpyrimidine
(Compound No. 47)

To 3.6 g (0.025 mole) of 4-chloro-5,6-dimethylpyrimidine were added 3.4 g (0.025 mole) of p-isopropylaniline; the mixture was then heated at 100°–150° C. for about 3 minutes. The reaction mixture quickly became a solution and soon produced a precipitate, which was separated and then made alkaline by the addition of 50 ml of a dilute aqueous solution of sodium hydroxide. The mixture was then extracted with ethyl acetate and the extract was washed, in turn, with water and with a saturated aqueous solution of sodium chloride. It was then dried over anhydrous sodium sulphate and then the ethyl acetate was distilled off under reduced pressure, to give crystals, which, on recrystallisation from a 3:1 by volume mixture of benzene and hexane, gave 1.4 g (yield 23%) of the desired product in the form of very fine colourless needles melting at 132°–133° C.

Elemental analysis: Calculated for $C_{15}H_{19}N_3$: C, 74.69%; H, 7.88%; N, 17.43%. Found: C, 75.00%; H, 7.90%; N, 17.70%.

EXAMPLE 6

5,6-Dimethyl-4-(4-trifluoromethylanilino)pyrimidine
(Compound No. 38)

To 4.3 g (0.03 mole) of 4-chloro-5,6-dimethylpyrimidine were added 4.8 g (0.03 mole) of p-aminobenzotrifluoride; the mixture was then heated at 100°–150° C. for about 3 minutes. The reaction mixture quickly became a solution and soon produced a precipitate which was separated and then made alkaline by the addition of 50 ml of a dilute aqueous solution of sodium hydroxide. The insolubles were collected by filtration, washed with water and then recrystallised from a 7:3 by volume mixture of ethanol and water, to give 1.2 g (yield 24%) of the desired Compound No. 38 in the form of a pale brown powder melting at 137°–139° C.

Elemental analysis: Calculated for $C_{13}H_{12}N_3F_3$: C, 58.42%; H, 4.53%; N, 15.72%. Found: C, 58.51%; H, 4.40%; N, 15.64%.

Following the procedures described in Examples 3–6, the compounds listed in Table 4 were also produced.

TABLE 4

| Compound No | melting at (°C.) or refractive index | Appearance | yield (%) |
|---|---|---|---|
| 22 | 150–153 | colourless needles | 38 |
| 24 | 184–186 | colourless needles | 81 |
| 26 | 115–117 | brown powder | 43 |
| 27 | 184–187 | colourless needles | 68 |
| 28 | 175–178 | yellowish-white prisms | 58 |
| 29 | 126–128 | yellow prisms | 47 |
| 30 | 143–145 | yellow-brown very fine needles | 69 |
| 31 | 137–139 | colourless needles | 69 |
| 32 | 188–191 | dark brown granules | 20 |
| 33 | 164–167 | yellow needles | 48 |
| 34 | 167–170 | yellow needles | 75 |
| 36 | 157–161 | colourless very fine needles | 66 |
| 37 | 167–169 | yellow powder | 67 |
| 39 | 134–136 | colourless prisms | 43 |
| 40 | 147–149 | black needles | 78 |
| 41 | 143–145 | yellow plates | 78 |
| 42 | 142–144 | brown powder | 66 |
| 43 | 119–120 | brown powder | 64 |
| 44 | 151–153 | yellow-brown prisms | 56 |

TABLE 4-continued

| Compound No | melting at (°C.) or refractive index | Appearance | yield (%) |
|---|---|---|---|
| 45 | 155–158 | colourless needles | 31 |
| 49 | 78–80 | brown powder | 81 |
| 50 | 136–139 | yellow powder | 6 |
| 52 | 202–204 | colourless needles | 27 |
| 55 | 193–195 | yellow sand | 39 |
| 57 | $n_D^{25}1.5938$ | brown oil | 83 |
| 58 | $n_D^{25}1.5862$ | brown oil | 74 |
| 59 | $n_D^{19}1.5869$ | brown oil | 13 |
| 60 | 74–76 | brown plates | 11 |
| 61 | 121–123 | yellow prisms | 45 |
| 62 | 138–139 | colourless needles | 74 |
| 63 | 149–151 | brown prisms | 71 |
| 64 | 128–131 | brown prisms | 69 |
| 65 | 94–97 | yellow-brown powder | 75 |
| 66 | 126–128 | brown prism | 55 |
| 67 | 125–127 | colourless plates | 49 |
| 68 | 103–105 | yellow prisms | 69 |
| 69 | 140–142 | brown needles | 59 |

EXAMPLE 7

4-Anilino-5,6-dimethylpyrimidine hydrochloride
(Compound No. 23)

To 4.3 g (0.03 mole) of 4-chloro-5,6-dimethylpyrimidine were added 2.8 g (0.03 mole) of aniline; the mixture was then heated at 100°–150° C. for about 3 minutes. The reaction mixture quickly became a solution and soon produced a precipitate, which was collected by filtration and then recrystallised from ethanol to give 3.2 g (yield 40%) of the desired Compound No. 23, in the form of a colourless powder melting at 243°–245° C.

Elemental analysis: Calculated for $C_{12}H_{14}N_3Cl$: C, 61.16%; H, 5.94%; N, 17.83%. Found: C, 61.40%; H, 6.00%; N, 18.00%.

Following the procedure described in Example 7, the compounds listed in Table 5 were also produced.

TABLE 5

| Compound No | melting at (°C.) | Appearance | yield (%) |
|---|---|---|---|
| 7 | 202–204 | colourless granules | 36 |
| 13 | 239–241 | pale orange needles | 21 |
| 35 | >270 | colourless powder | 44 |
| 48 | 245–247 | yellow powder | 90 |
| 54 | >270 | yellow needles | 21 |
| 71 | >270 | yellow prisms | 53 |

EXAMPLE 8

Capsules

The following powders (total weight 280 mg) were blended:

| | |
|---|---|
| 4-(4-bromoanilino)-5,6-dimethylpyrimidine (Compound No. 28) | 25.0 mg |
| lactose | 153.6 mg |
| corn starch | 100.0 mg |
| magnesium stearate | 1.4 mg |

The mixed powders were then passed through a screen with a 60 Tyler standard mesh and then placed in a No. 3 gelatin capsule.

EXAMPLE 9

Tablets

The following powders (total weight 120 mg) were formulated to produce a tablet by conventional means:

| | |
|---|---|
| 4-(4-bromoanilino)-6,7-dihydro-5H-cyclopental[d]pyrimidine (Compound No. 5) | 10.0 mg |
| lactose | 83.3 mg |
| corn starch | 25.0 mg |
| hydroxypropyl cellulose (a product of Nippon Soda Co., Ltd.) | 1.2 mg |
| magnesium stearate | 0.5 mg |

We claim:

1. Compounds of formula (I):

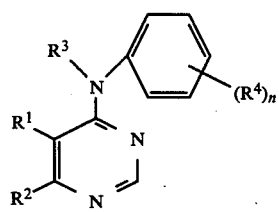

(wherein:
$R^1$ and $R^2$ are the same or different and each represents a $C_1$–$C_6$ alkyl group or $R^1$ and $R^2$ together represent a $C_3$–$C_5$ alkylene group;
$R^3$ represents a hydrogen atom or a $C_1$–$C_6$ alkyl group;
n is 0, 1 or 2; and
$R^4$ represents a $C_1$–$C_6$ alkyl group, a $C_1$–$C_6$ alkoxy group, a $C_1$–$C_6$ haloalkyl group, a halogen atom, a nitro group, a $C_1$–$C_6$ alkanesulphonyl group, a cyano group, a carboxy group or a $C_2$–$C_7$ alkoxycarbonyl group and, when n is 2, the two groups represented by $R^4$ may be the same or different or they may together represent a methylenedioxy group)
and pharmaceutically acceptable acid addition salts thereof.

2. Compounds as claimed in claim 1, wherein:
$R^1$ and $R^2$ are the same or different and each represents an alkyl group having from 1 to 4 carbon atoms or $R^1$ and $R^2$ together represent an alkylene group having 3 or 4 carbon atoms;
$R^3$ represents a hydrogen atom or an alkyl group having from 1 to 3 carbon atoms;
n is 0, 1 or 2; and
$R^4$ represents an alkyl group having from 1 to 4 carbon atoms, an alkoxy group having from 1 to 4 carbon atoms, a trifluoromethyl group, a halogen atom, a nitro group, an alkanesulphonyl group having from 1 to 3 carbon atoms, a cyano group, a carboxy group or an alkoxycarbonyl group having from 2 to 4 carbon atoms or, when n is 2, the two symbols $R^4$ may together represent a methylenedioxy group.

3. Compounds as claimed in claim 1, wherein:
$R^1$ represents a methyl group, an ethyl group or a butyl group and $R^2$ represents a methyl group, or $R^1$ and $R^2$ together represent a trimethylene group;
$R^3$ represents a hydrogen atom;
n is 0, 1 or 2; and
when n is 1, $R^4$ is at the 4-position of the benzene ring and represents an ethyl group, an isopropyl group, a trifluoromethyl group, a fluorine atom, a chlorine atom, a bromine atom, an iodine atom, a nitro group, a methanesulphonyl group, a cyano group, a carboxy group, a methoxycarbonyl group or an ethoxycarbonyl group, or
when n is 2, the two symbols $R^4$ are at the 3 and 4 positions of the benzene ring and each represents a chlorine atom.

4. Compounds as claimed in claim 1, wherein:
$R^1$ represents a methyl group, an ethyl group or a butyl group and $R^2$ represents a methyl group, or $R^1$ and $R^2$ together represent a trimethylene group;
$R^3$ represents a hydrogen atom;
n is 0 or 1; and
when n is 1, $R^4$ is at the 4-position of the benzene ring and represents an ethyl group, an isopropyl group, a fluorine atom, a chlorine atom, a bromine atom, an iodine atom, a cyano group or a methanesulphonyl group.

5. 4-(4-Cyanoanilino)-6,7-dihydro-5H-cyclopenta[d]pyrimidine and pharmaceutically acceptable acid addition salts thereof.

6. 4-(4-Bromoanilino)-5,6-dimethylpyrimidine and pharmaceutically acceptable acid addition salts thereof.

7. 4-(4-Bromoanilino)-5-n-butyl-6-methylpyrimidine and pharmaceutically acceptable acid addition salts thereof.

8. A pharmaceutical composition comprising an effective amount of an antidepressant compound in admixture with a pharmaceutically acceptable carrier or diluent, wherein the antidepressant compound is selected from compounds of formula (I):

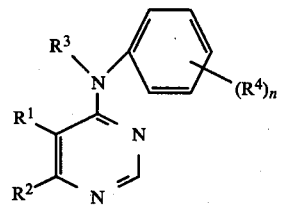

(wherein:
$R^1$ and $R^2$ are the same or different and each represents a $C_1$–$C_6$ alkyl group or $R^1$ and $R^2$ together represent a $C_3$–$C_5$ alkylene group;
$R^3$ represents a hydrogen atom or a $C_1$–$C_6$ alkyl group;
n is 0, 1 or 2; and
$R^4$ represents a $C_1$–$C_6$ alkyl group, a $C_1$–$C_6$ alkoxy group, a $C_1$–$C_6$ haloalkyl group, a halogen atom, a nitro group, a $C_1$–$C_6$ alkanesulphonyl group, a cyano group, a carboxy group or a $C_2$–$C_7$ alkoxycarbonyl group and, when n is 2, the two groups represented by $R^4$ may be the same or different or they may together represent a methylenedioxy group)
and pharmaceutically acid addition salts thereof.

9. A composition as claimed in claim 8, wherein said antidepressant compound is 4-(4-cyanoanilino)-6,7-dihydro-5Hcyclopenta[d]pyrimidine or a pharmaceutically acceptable acid addition salt thereof.

10. A composition as claimed in claim 8, wherein said antidepressant compound is 4-(4-bromoanilino)-5,6-dimethylpyrimidine or a pharmaceutically acceptable acid addition salt thereof.

11. A composition as claimed in claim 8, wherein said antidepressant compound is 4-(4-bromoanilino)-5-n-butyl-6-methylpyrimidine or a pharmaceutically acceptable acid addition salt thereof.

* * * * *